United States Patent [19]

Haga et al.

[11] Patent Number: 4,985,449

[45] Date of Patent: Jan. 15, 1991

[54] N-BENZOYL-N-PYRIDYLOXY PHENYL UREA COMPOUNDS AND PESTICIDE COMPOSITIONS CONTAINING THEM

[75] Inventors: Takahiro Haga; Tadaaki Toki; Toru Koyanagi; Yasuhiro Fujii; Kiyomitsu Yoshida; Osamu Imai, all of Kusatsu, Japan

[73] Assignee: Ishihara Sangyo Kaisha Ltd., Osaka, Japan

[21] Appl. No.: 365,607

[22] Filed: Jun. 13, 1989

Related U.S. Application Data

[62] Division of Ser. No. 102,855, Sep. 30, 1987, Pat. No. 4,861,799.

[30] Foreign Application Priority Data

Oct. 3, 1986 [JP] Japan .................. 61-235857
Mar. 11, 1987 [JP] Japan .................. 62-56006
Jun. 5, 1987 [JP] Japan .................. 62-141214

[51] Int. Cl.$^5$ .................. C07D 213/64; A01N 43/40
[52] U.S. Cl. .................. 514/349; 514/344; 514/345; 514/351; 514/352; 514/357; 546/286; 546/287; 546/288; 546/289; 546/294; 546/295; 546/296; 546/297; 546/300; 546/307; 546/312; 546/329; 546/334
[58] Field of Search .......... 546/286, 287, 288, 289, 546/294, 295, 296, 297, 300, 307, 312, 329, 334; 514/344, 345, 349, 351, 352, 357

[56] References Cited

U.S. PATENT DOCUMENTS

| | | | |
|---|---|---|---|
| 3,748,356 | 7/1973 | Wellinga et al. | 71/88 |
| 4,173,637 | 11/1979 | Nishiyama et al. | 514/349 |
| 4,173,638 | 11/1979 | Nishiyama et al. | 514/351 |
| 4,310,530 | 1/1982 | Nishiyama et al. | 514/351 |

FOREIGN PATENT DOCUMENTS

| | | | |
|---|---|---|---|
| 0094241 | 12/1977 | Poland | 564/88 |
| 0147676 | 11/1978 | Poland | 564/88 |
| 0139863 | 9/1987 | Poland | 564/88 |
| 0139504 | 4/1988 | Poland | 564/88 |
| 0098245 | 12/1988 | Poland | 564/88 |
| 145321 | 12/1988 | Poland | 564/88 |

OTHER PUBLICATIONS

Chemical Abstracts, vol. 102, No. 3, Abstract 24,486p, p. 681, Jan. 21, 1985, Chou.

*Primary Examiner*—Mary C. Lee
*Assistant Examiner*—Zinna Northington-Davis
*Attorney, Agent, or Firm*—Oblon, Spivak, McClelland, Maier & Neustadt

[57] ABSTRACT

A benzoylurea compound having the formula:

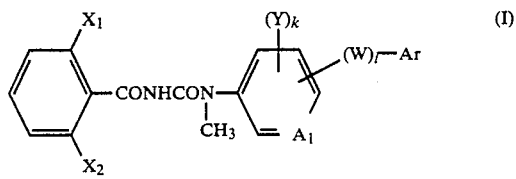

wherein each of $X_1$ and $X_2$ is a hydrogen atom, a halogen atom or a methyl group, provided that $X_1$ and $X_2$ are not simultaneously hydrogen atoms, Y is independently a hydrogen atom, a halogen atom, an alkyl group which may be substituted by halogen, a $-CO_2R_1$ group wherein $R_1$ is a hydrogen atom, a cation or an alkyl group, or a $-OR_1$ group wherein $R_1$ is as defined above, $A_1$ is =N— or

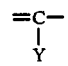

wherein Y is as defined above, W is an oxygen atom, a sulfur atom or

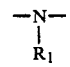

wherein $R_1$ is as defined above, k is an integer of from 1 to 3, l is 0 or 1, and Ar is

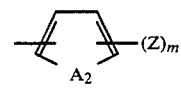

wherein Z is independently a hydrogen atom, a halogen atom, an alkyl group which may be substituted by halogen, an alkoxy group which may be substituted by halogen, a nitro group, a cyano group or a $-S(O)_nR_2$ group wherein $R_2$ is an alkyl group which may be substituted by halogen and n is 0, 1 or 2, $A_2$ is —S—,

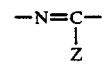

wherein Z is as defined above, or

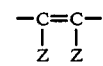

wherein Z is as defined above, and m is an integer of from 1 to 3, or a salt thereof.

9 Claims, No Drawings

4,985,449

N-BENZOYL-N-PYRIDYLOXY PHENYL UREA COMPOUNDS AND PESTICIDE COMPOSITIONS CONTAINING THEM

This is a division of application Ser. No. 07/102,855, filed on Sept. 30, 1987, now U.S. Pat. No. 4,861,799.

The present invention relates to novel benzoylurea compounds, a process for their production and pesticides containing them.

Benzoylurea compounds are known to be effective as insecticides, for example, from U.S. Pat. Nos. 3,748,356, 4,173,637, 4,173,638, 4,310,530 and 4,005,223. Further, derivatives of such benzoylurea compounds wherein the nitrogen atom in the urea moiety bonded to an aromatic ring is substituted by an alkyl group, are known, for example, from, U.S. Pat. Nos. 3,748,356, 4,607,044 and 4,659,736, Japanese Unexamined Patent Publications No. 184151/1984 and No. 106069/1987, PCT(JP) Publication No. 501418/1987, and J. Agr. Food Chem., Vol. 21, No. 3, 348-354 (1973). Furthermore, specific benzoylurea compounds wherein the above-mentioned nitrogen atom is substituted by an alkyl group and the above-mentioned aromatic ring is substituted by an aromatic ring are also broadly covered by the general formulas disclosed in the above publications. However, such specific benzoylurea compounds are not specifically disclosed in such publications.

The present invention is based on a discovery that among such specific benzoylurea compounds, those wherein the nitrogen atom in the urea moiety bonded to an aromatic ring is substituted by a methyl group, the other nitrogen atom bonded to the benzoyl group has a hydrogen atom and said aromatic ring contains an aromatic ring as a substituent, are highly safe to beneficial aquatic Crustacea and capable of being readily decomposed in soil, while exhibiting equal or superior insecticidal activities to those wherein the nitrogen atom in the urea moiety bonded to the aromatic ring is not substituted by a methyl group and has a hydrogen atom.

Thus, the present invention provides a benzoylurea compound having the formula:

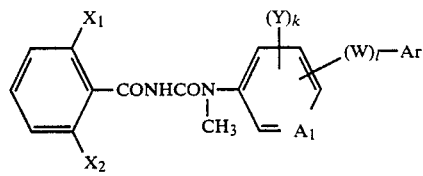

wherein each of $X_1$ and $X_2$ is a hydrogen atom, a halogen atom or a methyl group, provided that $X_1$ and $X_2$ are not simultaneously hydrogen atoms, Y is independently a hydrogen atom, a halogen atom, an alkyl group which may be substituted by halogen, a $-CO_2R_1$ group wherein $R_1$ is a hydrogen atom, a cation or an alkyl group, or a $-OR_1$ group wherein $R_1$ is as defined above, $A_1$ is $=N-$ or

wherein Y is as defined above, W is an oxygen atom, a sulfur atom or

wherein $R_1$ is as defined above, k is an integer of from 1 to 3, l is 0 or 1, and Ar is

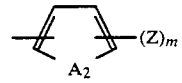

wherein Z is independently a hydrogen atom, a halogen atom, an alkyl group which may be substituted by halogen, an alkoxy group which may be substituted by halogen, a nitro group, a cyano group or a $-S(0)_nR_2$ group wherein $R_2$ is an alkyl group which may be substituted by halogen and n is 0, 1 or 2, $A_2$ is $-S-$,

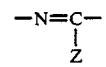

wherein Z is as defined above, or

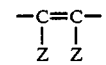

wherein Z is as defined above, and m is an integer of from 1 to 3, or a salt thereof.

Further, the present invention provides a process for producing the compound of the formula I, a pesticide containing the compound of the formula I and an intermediate useful for the production of the compound of the formula I.

Now, the present invention will be described in detail with reference to the preferred embodiments.

In connection with the formula I, the alkyl group, the alkyl group which may be substituted by halogen or the alkyl moiety in the alkoxy group which may be substituted by halogen, may be an alkyl group having from 1 to 6 carbon atoms such as a methyl group, an ethyl group, a n-propyl group, an isopropyl group, a n-butyl group, an isobutyl group or a sec-butyl group, preferably a methyl group or an ethyl group, more preferably a methyl group. The halogen atom or the halogen contained in the alkyl or alkoxy group which may be substituted by halogen, includes a fluorine atom, a chlorine atom, a bromine atom and an iodine atom, and it is preferably a fluorine atom, a chlorine atom or a bromine atom. The alkyl or alkoxy group which is substituted by halogen, may contain one or more halogen atoms. When it contains two or more halogen atoms, such halogen atoms may be the same or different.

The salt of the benzoylurea compound of the formula I is a salt at the nitrogen atom of the urea moiety, and may be a salt with an alkali metal atom.

Among the compounds of the formula I, preferred are those wherein (W)l is located at the m- or p-position, preferably p-position relative to the position to which the urea moiety is attached, while (W)l is attached to Ar at the position adjacent to $A_2$. The preferred compounds may be represented by the formula:

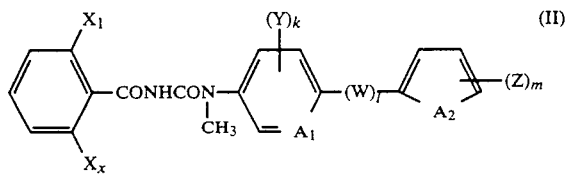

wherein $X_1$, $X_2$, Y, $A_1$, W, k, l, Z, $A_2$ and m are as defined above, or a salt thereof.

Each of $X_1$ and $X_2$ is preferably a hydrogen atom or a halogen atom, provided at least one of them is a halogen atom. Y is preferably independently a hydrogen atom, a halogen atom, an alkyl group which may be substituted by halogen, or a —$CO_2R_1$ group wherein $R_1$ is as defined above, and $A_1$ is preferably

wherein Y is as defined above. Z is preferably independently a hydrogen atom, a halogen atom, a trifluoromethyl group, a trifluoromethoxy group or a —$S(O)_nCF_3$ group wherein n is as defined above, and $A_2$ is preferably

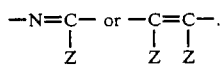

Specific preferred compounds will be given below:

N-[3,5-dichloro-4-(3-chloro-5-trifluoromethyl-2-pyridyloxy)phenyl]-N'-(2,6difluorobenzoyl)-N-methylurea, N-[4-(3-chloro-5-trifluoromethyl-2-pyridyloxy)-2,3 -difluorophenyl]-N'-(2,6, -difluorobenzoyl)-N-methylurea, N-[3-chloro-4-(3-chloro-5-trifluoromethyl-2-pyridyloxy)-phenyl]-N'-(2,6-difluorobenzoyl)-N-methylurea,
N-[4-(3-chloro-5-trifluoromethyl-2-pyridyloxy)-2,5-dimethylphenyl]-N'-(2,6-difluorobenzoyl)-N-methylurea, N-[3-chloro-4-(3-chloro-5-trifluoromethyl-2-pyridyloxy)-2-fluorophenyl]-N'-(2,6-difluorobenzoyl)-N-methylurea, N-[4-(3 -chloro-5-trifluoromethyl-2-pyridyloxy)-phenyl]-N'-(2-chlorobenzoyl)-N-methylurea, N-[4-(2-chloro-4-trifluoromethylphenoxy)-2,3-difluorophenyl]-N'-(2,6-difluorobenzoyl)-N-methylurea, N-[3-chloro-4-(2-chloro-4-trifluoromethylphenoxy)-phenyl]-N'-(2,6-difluorobenzoyl)-N-methylurea, N-[3-chloro-4-(2-chloro-4-trifluoromethylphenoxy)-2-fluorophenyl]-N'-(2,6-difluorobenzoyl)-N-methylurea, N-[4-(2-chloro-4-trifluoromethylphenoxy)phenyl]-N'-(2,6-difluorobenzoyl)-N-methylurea, N-[3-chloro-4-(2-chloro-4-trifluoromethylphenoxy)-phenyl]-N'-(2-chlorobenzoyl)-N-methylurea, N-[4-(3-chloro-5-trifluoromethyl-2-pyridyloxy)-2-methylphenyl]-N'-(2,6-difluorobenzoyl)-N-methylurea, N-{4-[3-chloro-5-trifluoromethyl-2-pyridyloxy]-3-fluorophenyl}-N'-(2,6-difluorobenzoyl)-N-methylurea, N-{4-[2-chloro-4-trifluoromethylphenoxy]-3-fluorophenyl}-N'-(2,6-difluorobenzoyl)-N-methylurea, N-{4-(2-chloro-4-trifluoromethylphenoxy)-3,5difluorophenyl}-N'-(2,6-difluorobenzoyl)-N-methylurea, N-{4-[2-chloro-4-trifluoromethylphenoxy]-3-methylphenyl}-N'-(2,6-difluorobenzoyl)-N-methylurea, N-{4-[3-chloro-5-trifluoromethyl-2-pyridyloxy]-3-methylphenyl}-N'-(2-chlorobenzoyl)-N-methylurea, N-[4'-chloro-2-fluoro-4biphenylyl)-N'-(2,6-difluorobenzoyl)-N-methylurea, N-(4'-bromo-4-biphenylyl)-N'-(2,6-difluorobenzoyl)-N-methylurea, N-(2,5-difluoro-4'-chloro-4-biphenylyl)-N'-(2,6-difluorobenzoyl)-N-methylurea, N-(2-trifluoromethyl-4'-chloro-4-biphenylyl)-N'-(2,6-difluorobenzoyl)-N-methylurea, N-(2,5-difluoro-3'-trifluoromethylthio-4-biphenylyl)-N'-(2,6-difluorobenzoyl)-N-methylurea.

The benzoylurea compound of the formula I of the present invention can be prepared, for example, by the following process.

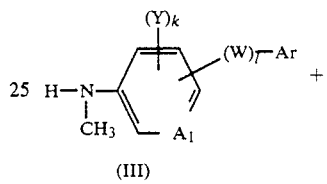

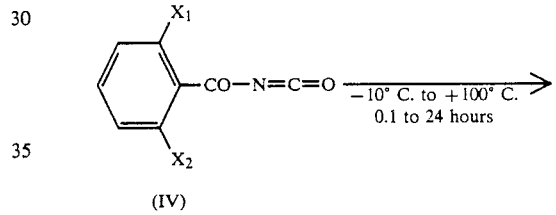

Compound of the formula I

In the above formulas, $X_1$, $X_2$, Y, k, $A_1$, W, l and Ar are as defined above.

The above reaction may be conducted in the presence of a solvent, if necessary. As such a solvent, an aromatic hydrocarbon such as benzene, toluene, xylene or chlorobenzene, a cyclic or non cyclic aliphatic hydrocarbon such as hexane or cyclohexane, an ether such as diethyl ether, dioxane or tetrahydrofuran, a nitrile such as acetonitrile or propionitrile, or an aprotic polar solvent such as dimethylformamide, dimethylsulfoxide, sulfolane or hexamethyl phosphoric acid triamide, may be mentioned.

The starting compound of the formula III can be prepared, for example, by the following process.

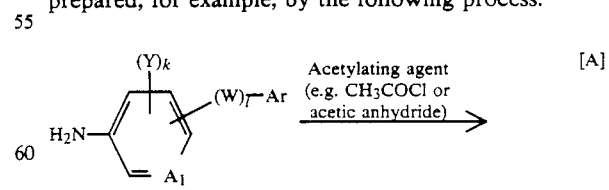

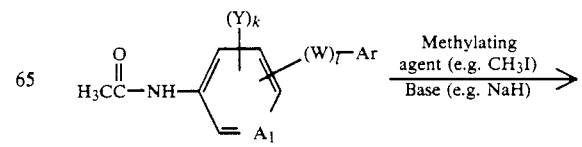

-continued

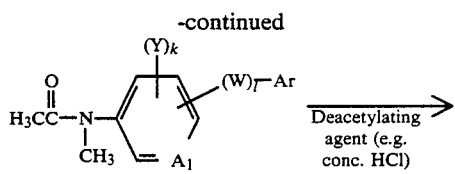

Compound of the formula (III)

In the above formulas, Y, k, $A_1$, W, l and Ar are as defined above.

Among the compounds of the formula III, those wherein l is 1 may be prepared, for example, also by the following process.

[B]

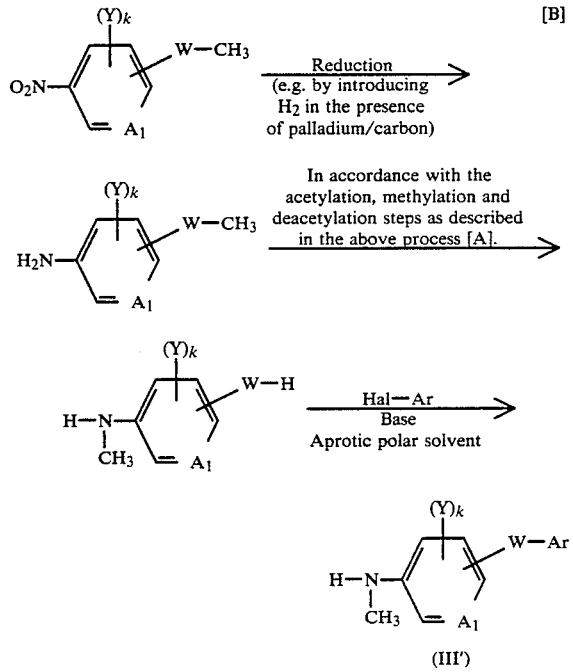

In the above formulas, Hal is a halogen atom, and Y, k, $A_1$, W and Ar are as defined above.

The reaction conditions for various reactions for the preparation of the starting compounds of the formulas III and III' such as the reaction temperature, reaction time, the solvent to be used as the case requires and the base, may be suitably selected from the reaction conditions commonly used for the reactions of this type.

The starting compound of the formula

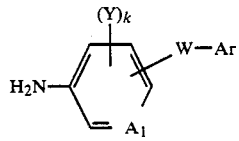

for process [A] can be prepared in the following manner.

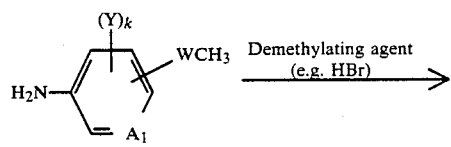

-continued

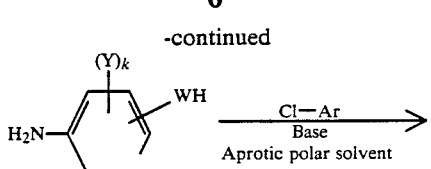

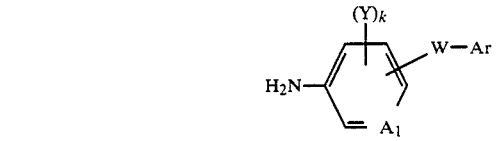

Now, specific Examples for the preparation of the intermediates for the compounds of the present invention will be described.

INTERMEDIATE PREPARATION EXAMPLE 1

Preparation of 4'-bromo-4-methylaminobiphenyl

[I] A solution prepared by dissolving 0.75 g of 4-amino-4'-bromobiphenyl in 10 ml of pyridine, was cooled with ice, and 1.0 g of acetyl chloride was dropwise added thereto. The mixture was stirred over a period of 30 minutes. After the completion of the reaction, the reaction solution was extracted with ethyl acetate and water. The organic layer was washed with dilute hydrochloric acid and further with a saturated sodium chloride aqueous solution, and then dried over anhydrous sodium sulfate. The solvent was distilled off under reduced pressure to obtain 0.8 g of N-(4'-bromo-4-biphenylyl)acetamide as colorless crystals.

[II] A solution prepared by dissolving 0.80 g of N-(4'-bromo-4-biphenylyl)acetamide obtained in step [I] in 10 ml of dimethylformamide, was dropwise added at a temperature of from 15° to 20° C. to 10 ml of a dimethylsulfoxide solution in which 0.17 g of sodium hydride (60% nujol mixture) was suspended. After the dropwise addition, the mixture was stirred at room temperature for 30 minutes, and then 0.78 g of methyl iodide was dropwise added thereto at a temperature of from 15° to 20° C. Then, the mixture was stirred for 3 hours at room temperature.

After the completion of the reaction, the reaction solution was extracted with ethyl acetate and water. The organic layer was washed with a saturated sodium chloride aqueous solution, and then dried over anhydrous sodium sulfate. Then, the solvent was distilled off under reduced pressure to obtain 0.76 g of N-(4'-bromo-4-biphenylyl)-N-methylacetamide as colorless crystals.

[III] 10 ml of concentrated hydrochloric acid was added to a solution prepared by dissolving 0.74 g of N-(4'-bromo-4-biphenylyl)-N-methylacetamide obtained in Step [II] in 20 ml of methanol, and the mixture was refluxed over a period of 18 hours.

After the completion of the reaction, the reaction solution was cooled and poured into 100 ml of a 10% potassium hydroxide aqueous solution. Then, it was extracted with methylene chloride. The organic layer was washed with water and further with a saturated sodium chloride aqueous solution, and then dried over anhydrous sodium sulfate. Then, the solvent was distilled off under reduced pressure, and the residue was purified by silica gel chromatography (developing solvent: n-hexane/ethyl acetate=4/1) to obtain 0.30 g of 4'-bromo-4-methylaminobiphenyl having a melting point of from 127 to 129° C.

INTERMEDIATE PREPARATION EXAMPLE 2

Preparation of 4-(3-chloro-5-trifluoromethyl-2-pyridyloxy)-3-fluoro(N-methyl)aniline 0.8 g of 4-(N-methyl)amino-2-fluorophenol prepared in the same manner as in Steps [I], [II] and [III] of Intermediate Preparation Example 1 by using 4-amino-2-fluoroanisol, 1.2 g of 2,3-dichloro-5-trifluoromethyl-pyridine and 0.9 g of anhydrous potassium carbonate were dissolved in 20 ml of dimethylsulfoxide, and reacted in a nitrogen stream at 100° C. for 1.5 hours.

After the completion of the reaction, the reaction solution was poured into ice water, and then extracted with ethyl ether. The organic layer was washed with water and further with a saturated sodium chloride aqueous solution, and then dried over anhydrous sodium sulfate. Then, the ethyl ether was distilled off under reduced pressure, and the residue was purified by silica gel chromatography (developing solvent: n-hexane/ethyl acetate =3/2) to obtain 0.5 g of 4-(3-chloro-5-trifluoromethyl-2-pyridyloxy)-3-fluoro(N-methyl)aniline.

INTERMEDIATE PREPARATION EXAMPLE 3

Preparation of 4-(2-chloro-4-trifluoromethyl-phenoxy)-3-fluoro(N-methyl)aniline

[I] 2 g of 5% palladium carbon was added to a solution prepared by dissolving 10 g of 4-nitro-2-fluoroanisol in 150 ml of 1,4-dioxane, and the mixture was subjected to catalytic reduction under a hydrogen gas pressure of 4 kg/cm$^2$ at room temperature for 30 minutes. After the completion of the reaction, palladium carbon was removed by filtration, and the solvent was distilled off under reduced pressure to obtain 8.6 g of 4-amino-2-fluoroanisol.

[II] 8.5 g of 4-amino-2-fluoroanisol obtained in Step [I] and 100 ml of hydrobromic acid (47%) were mixed, and the mixture was stirred under heating at 90° C. for 8 hours.

After the completion of the reaction, excess hydrobromic acid was distilled off under reduced pressure, and the residue was neutralized by an addition of an aqueous sodium hydrogen carbonate solution and extracted with ethyl acetate. The organic layer was washed with a saturated sodium chloride aqueous solution and dried over anhydrous sodium sulfate. Then, ethyl acetate was distilled off under reduced pressure to obtain 7.3 g of 4-amino-2-fluorophenol.

[III] 2.8 g of sodium hydride (60% nujol mixture) was gradually added under cooling with ice to a solution prepared by dissolving 7.3 g of 4-amino-2-fluorophenol obtained in Step [II] in 100 ml of hexamethyl phosphoric triamide. After the addition, the liquid temperature was returned to room temperature, and stirring was continued for 20 minutes. Then, to this solution, 13.6 g of 3,4-dichlorobenzotrifluoride was added, and the solution was heated to 70° C. and reacted for 40 minutes.

After the completion of the reaction, the reaction mixture was poured into ice water and extracted with ethyl acetate. The organic layer was washed with water and a saturated sodium chloride aqueous solution, and dried over anhydrous sodium sulfate. Then, ethyl acetate was distilled off under reduced pressure, and the residue was purified by silica gel chromatography (developing solvent: n-hexane/ethyl acetate =3/1) to obtain 10.4 g of 4-(2-chloro-4-trifluoromethylphenoxy)-3-fluoroaniline having a melting point of from 50° to 51° C.

[IV] By using 4-(2-chloro-4-trifluoromethylphenoxy)-3-fluoroaniline obtained in Step [III], 4-(2-chloro-4-trifluoromethylphenoxy)-3-fluoro(N-methyl)-aniline having a refractive index $n_D^{27.6}=1.5424$ was obtained in the same manner as in Steps [I], [II] and [III] of Intermediate Preparation Example I.

Typical Examples of the compounds of the formula III prepared in the same manner as in the foregoing Intermediate Preparation Examples are shown in Table 1.

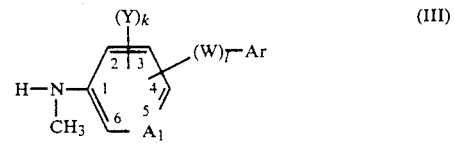
(III)

TABLE 1

| Intermediate No. | (Y)$_k$ | (W)$_l$ Position | W | l | A$_1$ | Ar | Physical properties |
|---|---|---|---|---|---|---|---|
| 1 | 3-F | 4 | O | 1 | =CH— | 5-trifluoromethyl-2-pyridyl | mp. 98–99° C. |
| 2 | 3-F | 4 | O | 1 | =CH— | 2-chloro-4-trifluoromethylphenyl | mp. 50–51° C. |
| 3 | 3-CO$_2$CH$_3$ | 4 | O | 1 | =C—<br>\|<br>CH$_3$ | 5-trifluoromethyl-2-pyridyl | mp. 99–100° C. |
| 4 | 3-F | 4 | O | 1 | =CH— | 2,4-dibromophenyl | $n_D^{18.2}$1.5633 |
| 5 | 3-F | 4 | O | 1 | =CH— | 4-trifluoromethylphenyl | $n_D^{18.2}$1.5319 |
| 6 | 3,6-F$_2$ | 4 | — | 0 | =CH— | 5-bromo-2-thienyl | mp. 74–77° C. |
| 7 | 2-CH$_3$ | 4 | O | 1 | =CH— | 2-fluoro-4-nitrophenyl | mp. 112–113° C. |
| 8 | 3-CH$_3$ | 4 | O | 1 | =C—<br>\|<br>CH$_3$ | 2-chloro-4-trifluoromethylphenyl | mp. 83–84° C. |

TABLE 1-continued

| Intermediate No. | (Y)$_k$ | (W)$_l$ Position | W | l | A$_1$ | Ar | Physical properties |
|---|---|---|---|---|---|---|---|
| 9 | 3-CH$_3$ | 4 | O | 1 | =C(CH$_3$)— | 3-chloro-5-trifluoromethyl-2-pyridyl | mp. 105° C. |
| 10 | 3-Cl | 4 | O | 1 | =C(Cl)— | 3-chloro-5-trifluoromethyl-2-pyridyl | mp. 146–147° C. |
| 11 | 2,3-F$_2$ | 4 | O | 1 | =CH— | 3-chloro-5-trifluoromethyl-2-pyridyl | Oil |
| 12 | 2,3-F$_2$ | 4 | O | 1 | =CH— | 2-chloro-4-trifluoromethylphenyl | mp. 37–38° C. |
| 13 | 2-F | 4 | O | 1 | =CH— | 3-chloro-5-trifluoromethyl-2-pyridyl | Oil |
| 14 | 2-F | 4 | O | 1 | =CH— | 2-chloro-4-trifluoromethylphenyl | Oil |
| 15 | 3-Cl | 4 | O | 1 | =CH— | 2-chloro-4-trifluoromethylphenyl | Oil |
| 16 | 2-F-3-Cl | 4 | O | 1 | =CH— | 2-chloro-4-trifluoromethylphenyl | Oil |
| 17 | 3-Cl | 4 | O | 1 | =CH— | 3-chloro-5-trifluoromethyl-2-pyridyl | Solid |
| 18 | — | 4 | — | 0 | =CH— | phenyl | Oil |
| 19 | — | 4 | — | 0 | =CH— | 4-bromophenyl | mp. 127–129° C. |
| 20 | — | 4 | O | 1 | =CH— | 2-chloro-4-trifluoromethylphenyl | mp. 62.5–63.5° C. |
| 21 | — | 4 | O | 1 | =CH— | 3-chloro-5-trifluoromethyl-2-pyridyl | Oil |
| 22 | 2-CH$_3$ | 4 | O | 1 | =CH— | 3-chloro-5-trifluoromethyl-2-pyridyl | Oil |
| 23 | 3,6-(CH$_3$)$_2$ | 4 | O | 1 | =CH— | 3-chloro-5-trifluoromethyl-2-pyridyl | mp. 75–78° C. |
| 24 | 3-Cl | 4 | O | 1 | =CH— | 2,4-dichlorophenyl | Oil |
| 25 | 3-Cl | 4 | O | 1 | =CH— | 4-nitrophenyl | mp. 70–72° C. |
| 26 | 2-F-3-Cl | 4 | O | 1 | =CH— | 3-chloro-5-trifluoromethyl-2-pyridyl | mp. 71–73° C. |
| 27 | — | 4 | O | 1 | =CH— | 3,5-dichloro-2-pyridyl | mp. 85–86° C. |
| 28 | — | 4 | O | 1 | =CH— | 5-chloro-3-trifluoromethyl-2-pyridyl | mp. 86–87° C. |
| 29 | — | 4 | O | 1 | =CH— | 2,3,4,5,6-pentafluorophenyl | Solid |
| 30 | — | 4 | O | 1 | =CH— | 2-chloro-4-nitrophenyl | mp. 124–125° C. |
| 31 | 3-CF$_3$ | 4 | O | 1 | =CH— | 3-chloro-5-trifluoromethyl-2-pyridyl | mp. 86–89° C. |
| 32 | — | 4 | S | 1 | =CH— | 3-chloro-5-trifluoromethyl-2-pyridyl | mp. 75–76° C. |

TABLE 1-continued

| Intermediate No. | (Y)$_k$ | (W)$_l$ Position | W | l | A$_1$ | Ar | Physical properties |
|---|---|---|---|---|---|---|---|
| 33 | 3-Cl | 4 | S | 1 | =C—<br>\|<br>Cl | 3-chloro-5-trifluoromethyl-2-pyridyl | mp. 137–138° C. |
| 34 | 3-F | 4 | O | 1 | =CH— | 3-chloro-5-trifluoromethyl-2-pyridyl | Solid |
| 35 | 3-Cl | 4 | O | 1 | =CH— | 3-chloro-5-trifluoromethyl-2-pyridyl | Oil |
| 36 | 3,6-F$_2$ | 4 | O | 1 | =CH— | 4-trifluoromethylphenyl | |
| 37 | 4-CH$_3$ | 3 | O | 1 | =CH— | 2-chloro-4-trifluoromethylphenyl | n$_D^{28.8}$1.5344 |
| 38 | 3-CH$_3$ | 4 | — | 0 | =CH— | 4-chlorophenyl | mp. 86–88° C. |
| 39 | — | 4 | — | 0 | =CH— | 2,4-dichlorophenyl | n$_D^{28.2}$1.5870 |
| 40 | — | 4 | — | 0 | =CH— | 4-chlorophenyl | mp. 117–118° C. |
| 41 | 2-CH$_3$ | 4 | — | 0 | =CH— | 4-bromophenyl | mp. 68–70° C. |
| 42 | 3,6-F$_2$ | 4 | — | 0 | =CH— | 4-trifluoromethylphenyl | Solid |
| 43 | 3-CO$_2$—CH$_3$ | 4 | O | 1 | =C—<br>\|<br>CH$_3$ | 3-chloro-5-trifluoromethyl-2-pyridyl | Oil |
| 44 | 3-CO$_2$—CH$_3$ | 4 | O | 1 | =CH— | 3-chloro-5-trifluoromethyl-2-pyridyl | Oil |
| 45 | 2,3,6-F$_3$ | 4 | O | 1 | =C—<br>\|<br>F | 3-chloro-5-trifluoromethyl-2-pyridyl | Oil |
| 46 | 3-CO$_2$—CH$_3$ | 4 | O | 1 | =CH— | 2-chloro-4-trifluoromethylphenyl | Oil |
| 47 | 6-F | 4 | — | 0 | =CH— | 4-chlorophenyl | Oil |
| 48 | 3-CF$_3$ | 4 | — | 0 | =CH— | 4-chlorophenyl | Oil |
| 49 | 3,6-F$_2$ | 4 | — | 0 | =CH— | 3-trifluoromethylthiophenyl | Oil |
| 50 | — | 4 | — | 0 | =N— | 4-chlorophenyl | Oil |
| 51 | 3-F | 4 | — | 0 | =CH— | 4-bromophenyl | Oil |
| 52 | — | 4 | — | 0 | =CH— | 5-bromo-2-thienyl | Oil |
| 53 | 3-CO$_2$H | 4 | O | 1 | =CH— | 2-chloro-4-trifluoromethylphenyl | |
| 54 | — | 4 | O | 1 | =CH— | 4-cyanophenyl | Oil |
| 55 | — | 4 | O | 1 | =CH— | 4-trifluoromethylthiophenyl | Oil |
| 56 | — | 4 | O | 1 | =CH— | 4-trifluoromethylsulfonylphenyl | Oil |
| 57 | 3-F | 4 | O | 1 | =CH— | phenyl | Oil |
| 58 | 3-OCH$_3$ | 4 | O | 1 | =CH— | 2-chloro-4-trifluoromethylphenyl | Oil |
| 59 | 3-CO$_2$H | 4 | O | 1 | =CH— | 3-chloro-5-trifluoromethyl-2- | |

TABLE 1-continued

| Intermediate No. | (Y)$_k$ | (W)$_l$ Position | W | l | A$_1$ | Ar | Physical properties |
|---|---|---|---|---|---|---|---|
| 60 | 3-OCH$_3$ | 4 | O | 1 | =CH— | 3-chloro-5-trifluoromethyl-2-pyridyl | Oil |
| 61 | 3-F | 4 | O | 1 | =CH— | 4-bromophenyl | Oil |
| 62 | — | 4 | O | 1 | =CH— | 2-fluoro-4-trifluoromethylphenyl | |
| 63 | — | 4 | O | 1 | =CH— | 3-fluoro-5-trifluoromethyl-2-pyridyl | |
| 64 | 3-F | 4 | O | 1 | =C(F)— | 3-chloro-5-trifluoromethyl-2-pyridyl | |
| 65 | 3-CO$_2$—CH$_3$ | 4 | — | 0 | =CH— | 4-bromophenyl | |
| 66 | — | 4 | — | 0 | =CH— | 4-methylphenyl | |
| 67 | — | 4 | — | 0 | =CH— | 4-trifluoromethoxyphenyl | |
| 68 | — | 4 | — | 0 | =CH— | 2,4,6-trichlorophenyl | |
| 69 | — | 4 | — | 0 | =CH— | 2,3,4,5,6-pentafluorophenyl | |
| 70 | 3,6-(CH$_3$)$_2$ | 4 | — | 0 | =CH— | 4-bromophenyl | |
| 71 | — | 4 | — | 0 | =CH— | 4-methoxyphenyl | |
| 72 | — | 4 | — | 0 | =CH— | 4-methylthiophenyl | |
| 73 | — | 4 | — | 0 | =CH— | 5-chloro-2-thienyl | |
| 74 | 3-Cl | — | O | 1 | =CH— | 4-methoxyphenyl | Oil |
| 75 | 4-CH$_3$ | 3 | O | 1 | =CH— | 2-chloro-4-trifluoromethylphenyl | Oil |
| 76 | — | 4 | O | 1 | =CH— | 4-trifluoromethoxyphenyl | |
| 77 | 3-CH$_3$ | 4 | O | 1 | =CH— | 2-chloro-4-trifluoromethoxyphenyl | |
| 78 | 3-CO$_2$—Na | 4 | O | 1 | =CH— | 2-chloro-4-trifluoromethylphenyl | |
| 79 | 3-CO$_2$—C$_2$H$_5$ | 4 | O | 1 | =CH— | 2-chloro-4-trifluoromethylphenyl | |
| 80 | 4-Cl | 3 | O | 1 | =CH— | 2-chloro-4-trifluoromethylphenyl | |
| 81 | — | 4 | O | 1 | =CH— | 2-chloro-5-trifluoromethyl-3-pyridyl | |
| 82 | — | 4 | —N(CH$_3$)— | 1 | =CH— | 3-chloro-5-trifluoromethyl-2-pyridyl | Oil |
| 83 | — | 4 | —N(CH$_3$)— | 1 | =CH— | 2-chloro-4-trifluoromethylphenyl | $n_D^{28.0}$ 1.5838 |

Now, specific Examples for the preparation of the compounds of the present invention will be described. However, it should be understood that the present invention is by no means restricted to these specific Examples.

Preparation of N-(4'-bromo-4-biphenylyl)-N'-(2,6difluorobenzoyl)-N-methylurea (Compound No. 29)

A solution prepared by dissolving 0.27 g of 2,6-difluorobenzoyl isocyanate in 5 ml of dioxane was added at room temperature to a solution prepared by dissolving 0.20 g of 4'-bromo-4-methylaminobiphenyl in 5 ml of dioxane, and the mixture was stirred at room temperature for 15 hours.

After the completion of the reaction, the reaction solution was poured into 100 ml of water, and precipitated crystals were collected by filtration and dried under reduced pressure. The solid thus obtained was suspended in 50 ml of ethyl ether. The insoluble substance was collected by filtration to obtain 0.26 g of N-(4'-bromo-4-biphenylyl)-N'-(2,6-difluorobenzoyl)-N-methylurea as crystals having a melting point of from 183° to 185° C.

PREPARATION EXAMPLES 2 to 9

In the same manner as in preparation Example 1, the compounds as identified in Table 2 were prepared by using the reagents and reaction conditions as identified in Table 2.

TABLE 2

| | Reagents | | Dioxane (solvent) | | Reaction condition | | Products: |
| | Starting materials | | Amount for dissolving aniline compound (ml) | Amount for dissolving benzoyl isocyanate compound (ml) | | | Compound of |
| Preparation Example No. | Aniline compound (g) | Benzoyl isocyanate compound (g) | | | Temp. (°C.) | Time (hr) | the present invention (g) |
| --- | --- | --- | --- | --- | --- | --- | --- |
| 2 | Intermediate No. 34 (0.48) | 2,6-difluoro-benzoyl isocyanate (0.55) | 0 | 15 | Room temp. | 2 | Compound No. 3 (0.68) |
| 3 | Intermediate No. 2 (3.0) | same as above (3.7) | 10 | 40 | Room temp. | 12 | Compound No. 4 (3.2) |
| 4 | Intermediate No. 15 (0.34) | same as above (0.6) | 5 | 5 | Room temp. | 1 | Compound No. 12 (0.42) |
| 5 | Intermediate No. 35 (0.16) | same as above (0.2) | 10 | 5 | Room temp. | 2 | Compound No. 15 (0.25) |
| 6 | Intermediate No. 20 (0.2) | 2,6-difluoro-benzoyl isocyanate (0.25) | 6 | 4 | Room temp. | 4 | Compound No. 18 (0.2) |
| 7 | Intermediate No. 21 (0.24) | same as above (0.3) | 5 | 5 | Room temp. | 4 | Compound No. 19 (0.3) |
| 8 | Intermediate No. 42 (0.95) | same as above (0.7) | 20 | 0 | Room temp. | 0.5 | Compound No. 24 (1.3) |
| 9 | Intermediate No. 10 (0.5) | same as above (0.8) | 5 | 5 | Room temp. | 4 | Compound No. 1 (0.72) |

Note: Intermediate Nos. in the column for "aniline compound" and Compounds Nos. in the column for "Product" are identified in Tables 1 and 3, respectively.

Typical examples of the compound of the present invention will be given in Table 3.

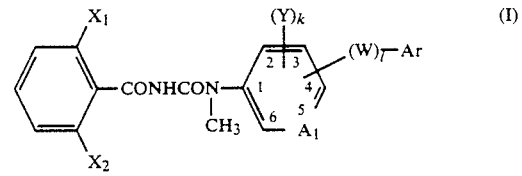

TABLE 3

| Compound No. | $X_1$ | $X_2$ | $(Y)_k$ | $(W)_l$ position | W | l | $A_1$ | Ar | Physical properties (°C.) | $^1$HNMR δ (ppm) (1*) |
| --- | --- | --- | --- | --- | --- | --- | --- | --- | --- | --- |
| 1 | F | F | 3-Cl | 4 | O | 1 | =C—<br>\|<br>Cl | 3-chloro-5-trifluoro-methyl-2-pyridyl | Amorphous solid mp. 85–92° C. | 3.28 (S, in CDCl$_3$) |
| 2 | F | F | 2,3-F$_2$ | 4 | O | 1 | =CH— | 3-chloro-5-trifluoro-methyl-2-pyridyl | mp. 175–178° C. | 3.25 (S, in CDCl$_3$) |
| 3 | F | F | 3-F | 4 | O | 1 | =CH— | 3-chloro-5-trifluoro-methyl-2-pyridyl | mp. 175–176° C. | 3.25 (S in CDCl$_3$) |

TABLE 3-continued

| Compound No. | $X_1$ | $X_2$ | $(Y)_k$ | (W)$_l$ position | W | l | $A_1$ | Ar | Physical properties (°C.) | $^1$HNMR δ (ppm) (1*) |
|---|---|---|---|---|---|---|---|---|---|---|
| 4 | F | F | 3-F | 4 | O | 1 | =CH— | 2-chloro-4-trifluoro-methylphenyl | Amorphous solid | 3.20 (S, in CCl$_4$) |
| 5 | F | F | 2,3-F$_2$ | 4 | O | 1 | =CH— | 2-chloro-4-trifluoro-methylphenyl | mp. 164–166° C. | 3.23 (S, in CDCl$_3$) |
| 6 | F | F | 3-CO$_2$—CH$_3$ | 4 | O | 1 | =C—<br>\|<br>CH$_3$ | 3-chloro-5-trifluoro-methyl-2-pyridyl | Amorphous solid | 3.21 (S, in CCl$_4$) |
| 7 | F | F | 3-CO$_2$—CH$_3$ | 4 | O | 1 | =C—<br>\|<br>CH$_3$ | 5-trifluoro-methyl-2-pyridyl | mp. 65–70° C. | 3.21 (S, in acetone-d$_6$) |
| 8 | F | F | 3-CO$_2$—CH$_3$ | 4 | O | 1 | =CH— | 3-chloro-5-trifluoro-methyl-2-pyridyl | Amorphous solid | 3.24 (S, in CCl$_4$) |
| 9 | F | F | 3-CO$_2$—CH$_3$ | 4 | O | 1 | =CH— | 5-trifluoro-methyl-2-pyridyl | Amorphous solid | 3.20 (S, in CCl$_4$) |
| 10 | F | F | 3-F | 4 | O | 1 | =CH— | 5-trifluoro-methyl-2-pyridyl | mp. 146–147° C. | 3.17 (S, in CCl$_4$) |
| 11 | F | F | 2,3,6-F$_3$ | 4 | O | 1 | =C—<br>\|<br>F | 3-chloro-5-trifluoro-methyl-2-pyridyl | mp. 173–176° C. | 3.30 (S, in CDCl$_3$) |
| 12 | F | F | 3-Cl | 4 | O | 1 | =CH— | 2-chloro-4-trifluoro-metylphenyl | Amorphous solid | 3.20 (S, in CDCl$_3$) |
| 13 | F | F | 2-F-3-Cl | 4 | O | 1 | =CH— | 2-chloro-4-trifluoro-metylphenyl | mp. 65–66° C. | 3.23 (S, in CDCl$_3$) |
| 14 | F | F | 3-CO$_2$—CH$_3$ | 4 | O | 1 | =CH— | 2-chloro-4-trifluoro-metylphenyl | Amorphous solid | 3.19 (S, in CCl$_4$) |
| 15 | F | F | 3-Cl | 4 | O | 1 | =CH— | 3-chloro-5-trifluoro-methyl-2-pyridyl | mp. 153–154° C. | 3.25 (S, in CDCl$_3$) |
| 16 | F | F | 2-F | 4 | O | 1 | =CH— | 2-chloro-4-trifluoro-methylphenyl | Amorphous solid | 3.21 (S, in CDCl$_3$) |
| 17 | F | F | 2-F | 4 | O | 1 | =CH— | 3-chloro-5-trifluoro-methyl-2-pyridyl | mp. 139–141° C. | |
| 18 | F | F | — | 4 | O | 1 | =CH— | 2-chloro-4-trifluoro-methylphenyl | mp. 129–131° C. | 3.22 (S, in CDCl$_3$) |
| 19 | F | F | — | 4 | O | 1 | =CH— | 3-chloro-5-trifluoro-methyl-2-pyridyl | mp. 147–149° C. | 3.28 (S, in CDCl$_3$) |
| 20 | F | F | 2-CH$_3$ | 4 | O | 1 | =CH— | 3-chloro-5-trifluoro-methyl-2-pyridyl | mp. 113–115° C. | 3.29 (S, in CDCl$_3$) |
| 21 | F | F | 2-F | 4 | — | 0 | =CH— | 4-chloro-phenyl | Amorphous solid | 3.15 (S, in CCl$_4$) |
| 22 | F | F | 2-F | 4 | — | 0 | =CH— | 4-trifluoro-methylphenyl | Amorphous solid | 3.18 (S, in CCl$_4$) |
| 23 | F | F | 3,6-F$_2$ | 4 | — | 0 | =CH— | 3-trifluoro-methylphenyl | mp. 170° C. | 3.19 (S, in CCl$_4$) |
| 24 | F | F | 3,6-F$_2$ | 4 | — | 0 | =CH— | 4-trifluoro-methylphenyl | Amorphous solid | 3.19 (S, in CCl$_4$) |
| 25 | F | F | 3,6-F$_2$ | 4 | — | 0 | =CH— | 4-chloro-phenyl | Amorphous solid | 3.19 (S, in CCl$_4$) |
| 26 | F | F | 3-CF$_3$ | 4 | — | 0 | =CH— | 4-chloro-phenyl | Amorphous solid | 3.25 (S, in CCl$_4$) |
| 27 | F | F | 3,6-F$_2$ | 4 | — | 0 | =CH— | 3-trifluoro-methylthio- | Amorphous solid | 3.16 (S, in CCl$_4$) |

TABLE 3-continued

| Compound No. | $X_1$ | $X_2$ | $(Y)_k$ | (W)$_l$ position | W | l | $A_1$ | Ar | Physical properties (°C.) | $^1$HNMR δ (ppm) (1*) |
|---|---|---|---|---|---|---|---|---|---|---|
| 28 | F | F | — | 4 | — | 0 | =CH— | phenyl | mp. 181–182° C. | |
| 29 | F | F | — | 4 | — | 0 | =CH— | 4-bromophenyl | mp. 183–185° C. | 3.29 (S, in DMSO-d$_6$) |
| 30 | F | F | — | 4 | — | 0 | =N— | 4-chlorophenyl | mp. 169–172° C. | 3.18 (S, in CCl$_4$) |
| 31 | F | F | 3-F | 4 | — | 0 | =CH— | 4-chlorophenyl | mp. 136–137° C. | 3.21 (S, in CCl$_4$) |
| 32 | F | F | 3-F | 4 | — | 0 | =CH— | 4-bromophenyl | Amorphous solid | 3.24 (S, in CCl$_4$) |
| 33 | F | F | — | 4 | — | 0 | =CH— | 5-bromo-2-thienyl | mp. 175–176° C. | 3.20 (S, in CCl$_4$) |
| 34 | F | F | 3,6-F$_2$ | 4 | — | 0 | =CH— | 5-bromo-2-thienyl | mp. 166–168° C. | 3.29 (S, in CCl$_4$) |
| 35 | Cl | H | — | 4 | O | 1 | =CH— | 3-chloro-5-trifluoromethyl-2-pyridyl | mp. 156–159° C. | 3.30 (S, in CDCl$_3$) |
| 36 | F | F | 3-F | 4 | O | 1 | =C—<br>  \|<br>  F | 2-chloro-4-trifluoromethylphenyl | mp. 150–152° C. | 3.28 (S, in CCl$_4$) |
| 37 | F | F | 3-CO$_2$H | 4 | O | 1 | =CH— | 2-chloro-4-trifluoromethylphenyl | mp. 96–98° C. | 3.22 (S, in CCl$_4$) |
| 38 | F | F | — | 4 | O | 1 | =CH— | 4-cyanophenyl | mp. 154–160° C. | 3.22 (S, in CCl$_4$) |
| 39 | F | F | — | 4 | O | 1 | =CH— | 4-trifluoromethylthiophenyl | Amorphous solid | 3.15 (S, in CCl$_4$) |
| 40 | F | F | — | 4 | O | 1 | =CH— | 4-trifluoromethylphenyl | mp. 138–139° C. | 3.13 (S, in CCl$_4$) |
| 41 | F | F | — | 4 | O | 1 | =CH— | 4-trifluoromethylsulfonylphenyl | mp. 148–152° C. | 3.20 (S, in CCl$_4$) |
| 42 | F | F | 3-F | 4 | O | 1 | =CH— | phenyl | mp. 113–114° C. | 3.19 (S, in CCl$_4$) |
| 43 | F | F | 3-Cl | 4 | O | 1 | =CH— | 2,4-dichlorophenyl | Amorphous solid | 3.20 (S, in CDCl$_3$) |
| 44 | F | F | 3-Cl | 4 | O | 1 | =CH— | 4-nitrophenyl | mp. 160–161° C. | 3.29 (S, in CDCl$_3$) |
| 45 | Cl | H | — | 4 | O | 1 | =CH— | 2-chloro-4-trifluoromethylphenyl | mp. 164–165° C. | 3.25 (S, in CDCl$_3$) |
| 46 | Cl | H | 3-Cl | 4 | O | 1 | =CH— | 2-chloro-4-trifluoromethylphenyl | mp. 131–133° C. | 3.28 (S, in CDCl$_3$) |
| 47 | F | F | 2-CH$_3$ | 4 | O | 1 | =CH— | 4-trifluoromethylphenyl | Amorphous solid | 3.09 (S, in CCl$_4$) |
| 48 | F | F | 3-F | 4 | O | 1 | =CH— | 2,4-dichlorophenyl | mp. 120° C. | 3.15 (S, in CCl$_4$) |
| 49 | F | F | 3-F | 4 | O | 1 | =CH— | 2,4-dibromophenyl | Amorphous solid | 3.19 (S, in CCl$_4$) |
| 50 | F | F | 3-F | 4 | O | 1 | =CH— | 4-trifluoromethylphenyl | mp. 120–121° C. | 3.19 (S, in CCl$_4$) |
| 51 | Cl | H | 3-F | 4 | O | 1 | =CH— | 4-trifluoromethylphenyl | Amorphous solid | 3.20 (S, in CCl$_4$) |
| 52 | Cl | H | 3-F | 4 | O | 1 | =CH— | 2,4-dibromophenyl | Amorphous solid | 3.20 (S, in CCl$_4$) |
| 53 | Cl | H | 3-F | 4 | O | 1 | =CH— | 2-chloro-4-trifluoromethylphenyl | Amorphous solid | 3.19 (S, in CCl$_4$) |
| 54 | F | F | 3-OCH$_3$ | 4 | O | 1 | =CH— | 2-chloro-4-trifluoromethylphenyl | Amorphous solid | 3.20 (S, in CCl$_4$) |
| 55 | Cl | H | 3-CH$_3$ | 4 | O | 1 | =CH— | 2-chloro-4-trifluoromethylphenyl | Amorphous solid | 3.19 (S, in CCl$_4$) |
| 56 | F | F | 2-CH$_3$ | 4 | O | 1 | =CH— | 2-fluoro-4-nitrophenyl | Amorphous solid | 3.05 (S, in CCl$_4$) |
| 57 | F | F | 3-CH$_3$ | 4 | O | 1 | =CH— | 2-chloro-4-trifluoromethylphenyl | Amorphous solid | 3.19 (S, in CCl$_4$) |
| 58 | Cl | Cl | — | 4 | O | 1 | =CH— | 2-chloro-4-trifluoromethylphenyl | mp. 139–140° C. | 3.20 (S, in CDCl$_3$) |

TABLE 3-continued

| Compound No. | $X_1$ | $X_2$ | $(Y)_k$ | $(W)_l$ position | W | l | $A_1$ | Ar | Physical properties (°C.) | $^1$HNMR δ (ppm) (1*) |
|---|---|---|---|---|---|---|---|---|---|---|
| 59 | F | H | — | 4 | O | 1 | =CH— | 2-chloro-4-trifluoro-methylphenyl | mp. 160-161° C. | |
| 60 | Br | H | — | 4 | O | 1 | =CH— | 2-chloro-4-trifluoro-methylphenyl | mp. 115-116° C. | |
| 61 | F | F | — | 4 | O | 1 | =CH— | pentafluoro-phenyl | mp. 133-135° C. | 3.20 (S, in CDCl$_3$) |
| 62 | F | F | — | 4 | O | 1 | =CH— | 2-chloro-4-nitrophenyl | mp. 136-140° C. | 3.25 (S, in CDCl$_3$) |
| 63 | CH$_3$ | H | 3-F | 4 | O | 1 | =CH— | 2-chloro-4-trifluoro-methylphenyl | mp. 124-126° C. | 3.29 (S, in CCl$_4$) |
| 64 | CH$_3$ | H | 3-CH$_3$ | 4 | O | 1 | =CH— | 2-chloro-4-trifluoro-methylphenyl | mp. 103-106° C. | 3.29 (S, in CCl$_4$) |
| 65 | F | F | 3-CH$_3$ | 4 | O | 1 | =C—<br>\|<br>CH$_3$ | 2-chloro-4-trifluoro-methylphenyl | Amorphous solid | 3.19 (S, in CCl$_4$) |
| 66 | CH$_3$ | H | 3-CH$_3$ | 4 | O | 1 | =C—<br>\|<br>CH$_3$ | 2-chloro-4-trifluoro-methylphenyl | Amorphous solid | 3.25 (S, in CCl$_4$) |
| 67 | F | F | 3-CO$_2$H | 4 | O | 1 | =CH— | 3-chloro-5-trifluoro-methyl-2-pyridyl | mp. 105° C. | 3.29 (S, in CCl$_4$ + DMSO-d$_6$) |
| 68 | F | F | 3-Cl | 4 | O | 1 | =C—<br>\|<br>Cl | 3-fluoro-5-trifluoro-methyl-2-pyridyl | mp. 167-169° C. | 3.25 (S, in CDCl$_3$) |
| 69 | F | F | 3,6-(CH$_3$)$_2$ | 4 | O | 1 | =CH— | 3-chloro-5-trifluoro-methyl-2-pyridyl | Amorphous solid | 3.19 (S, in CDCl$_3$) |
| 70 | F | F | 2-F-3-Cl | 4 | O | 1 | =CH— | 3-chloro-5-trifluoro-methyl-2-pyridyl | mp. 186-187° C. | 3.30 (S, in CDCl$_3$ + Acetone-d$_6$) |
| 71 | F | F | 3-CF$_3$ | 4 | O | 1 | =CH— | 3-chloro-5-trifluoro-methyl-2-pyridyl | Amorphous solid | 3.34 (S, in CDCl$_3$) |
| 72 | Cl | H | 3-Cl | 4 | O | 1 | =CH— | 3-chloro-5-trifluoro-methyl-2-pyridyl | mp. 161-162° C. | 3.32 (S, in Acetone-d$_6$ + DMSO-d$_6$) |
| 73 | F | F | — | 4 | O | 1 | =CH— | 3,5-dichloro-2-pyridyl | mp. 138-140° C. | 3.30 (S, in DMSO-d$_6$) |
| 74 | F | F | — | 4 | O | 1 | =CH— | 3-trifluoro-methyl-5-chloro-2-pyridyl | mp. 111-112° C. | 3.27 (S, in CDCl$_3$) |
| 75 | F | F | 3-OCH$_3$ | 4 | O | 1 | =CH— | 3-chloro-5-trifluoro-methyl-2-pyridyl | Amorphous solid | 3.21 (S, in CCl$_4$) |
| 76 | F | F | 3-CH$_3$ | 4 | O | 1 | =CH— | 3-chloro-5-trifluoro-methyl-2-pyridyl | mp. 178-179° C. | 3.25 (S, in CCl$_4$ + DMSO-d$_6$) |
| 77 | Cl | H | 3-CH$_3$ | 4 | O | 1 | =CH— | 3-chloro-5-trifluoro-methyl-2-pyridyl | Amorphous solid | 3.21 (S, in CCl$_4$) |
| 78 | Cl | Cl | — | 4 | O | 1 | =CH— | 3-chloro-5-trifluoro-methyl-2-pyridyl | mp. 155-156° C. | 3.24 (S, in CDCl$_3$) |
| 79 | F | H | — | 4 | O | 1 | =CH— | 3-chloro-5-trifluoro-methyl-2-pyridyl | mp. 176-177° C. | |

TABLE 3-continued

| Compound No. | $X_1$ | $X_2$ | $(Y)_k$ | (W)$_l$ position | W | l | $A_1$ | Ar | Physical properties (°C.) | $^1$HNMR δ (ppm) (1*) |
|---|---|---|---|---|---|---|---|---|---|---|
| 80 | Br | H | — | 4 | O | 1 | =CH— | 3-chloro-5-trifluoromethyl-2-pyridyl | mp. 135–136° C. | |
| 81 | CH$_3$ | H | — | 4 | O | 1 | =CH— | 3-chloro-5-trifluoromethyl-2-pyridyl | mp. 127–128° C. | 3.30 (S, in CDCl$_3$) |
| 82 | F | F | 3-CH$_3$ | 4 | O | 1 | =C—CH$_3$ | 3-chloro-5-trifluoromethyl-2-pyridyl | mp. 197–198° C. | 3.20 (S, in CCl$_4$) |
| 83 | CH$_3$ | H | 3-CH$_3$ | 4 | O | 1 | =C—CH$_3$ | 3-chloro-5-trifluoromethyl-2-pyridyl | mp. 96–97° C. | 3.22 (S, in CCl$_4$) |
| 84 | F | F | — | 4 | S | 1 | =CH— | 3-chloro-5-trifluoromethyl-2-pyridyl | mp. 123–124° C. | 3.29 (S, in CDCl$_3$) |
| 85 | F | F | 3-Cl | 4 | S | 1 | =C—Cl | 3-chloro-5-trifluoromethyl-2-pyridyl | mp. 167–168° C. | 3.30 (S, in CDCl$_3$) |
| 86 | F | F | 3-F | 4 | O | 1 | =CH— | 4-bromophenyl | mp. 119–120° C. | 3.20 (S, in CCl$_4$) |
| 87 | F | F | — | 4 | O | 1 | =CH— | 2-fluoro-4-trifluoromethylphenyl | | |
| 88 | Cl | Cl | 3-Cl | 4 | O | 1 | =C—Cl | 3-chloro-5-trifluoromethyl-2-pyridyl | | |
| 89 | Cl | H | 2,3-F$_2$ | 4 | O | 1 | =CH— | 2-chloro-4-trifluoromethylphenyl | | |
| 90 | Cl | H | — | 4 | O | 1 | =CH— | 3-fluoro-5-trifluoromethyl-2-pyridyl | | |
| 91 | F | H | 3-Cl | 4 | O | 1 | =C—Cl | 3-chloro-5-trifluoromethyl-2-pyridyl | | |
| 92 | F | H | 3-Cl | 4 | O | 1 | =CH— | 2-chloro-4-trifluoromethylphenyl | | |
| 93 | F | F | 3-F | 4 | O | 1 | =C—F | 3-chloro-5-trifluoromethyl-2-pyridyl | | |
| 94 | Cl | H | — | 4 | — | 0 | =CH— | 4-bromophenyl | | |
| 95 | F | F | 3-CH$_3$ | 4 | — | 0 | =CH— | " | | |
| 96 | F | F | 3-CO$_2$—CH$_3$ | 4 | — | 0 | =CH— | " | | |
| 97 | Cl | H | — | 4 | — | 0 | =CH— | 4-methylphenyl | | |
| 98 | F | F | — | 4 | — | 0 | =CH— | 4-trifluoromethoxyphenyl | | |
| 99 | Cl | H | — | 4 | — | 0 | =CH— | 2,4,6-trichlorophenyl | | |
| 100 | Cl | H | — | 4 | — | 0 | =CH— | 2,3,4,5,6-pentafluorophenyl | | |

TABLE 3-continued

| Compound No. | $X_1$ | $X_2$ | $(Y)_k$ | (W)$_l$ position | W | l | $A_1$ | Ar | Physical properties (°C.) | $^1$HNMR δ (ppm) (1*) |
|---|---|---|---|---|---|---|---|---|---|---|
| 101 | F | F | 3,6-$F_2$ | 4 | — | 0 | =CH— | 4-bromophenyl | | |
| 102 | Cl | H | 3,6-$(CH_3)_2$ | 4 | — | 0 | =CH— | " | | |
| 103 | F | F | — | 4 | — | 0 | =CH— | 4-methoxyphenyl | | |
| 104 | Cl | H | — | 4 | — | 0 | =CH— | 4-methylthiophenyl | | |
| 105 | F | F | — | 4 | — | 0 | =CH— | 5-chloro-2-thienyl | | |
| 106 | F | F | 3-$CO_2H$ | 4 | — | 0 | =CH— | 4-bromophenyl | | |
| 107 | F | F | 3-F | 4 | — | 0 | =CH— | " | | |
| 108 | F | F | — | 4 | — | 0 | =CH— | 4-trifluoromethylphenyl | mp. 171–174° C. | 3.29 (S, in $CDCl_3$) |
| 109 | F | F | 2-$CH_3$ | 4 | — | 0 | =CH— | 4-bromophenyl | mp. 167–169° C. | 3.12 (S, in $CCl_4$) |
| 110 | F | F | 3-Cl | 4 | O | 1 | =CH— | 4-methoxyphenyl | mp. 137–138° C. | 3.19 (S, in $CDCl_3$) |
| 111 | F | F | — | 4 | — | 0 | =CH— | 4-chlorophenyl | mp. 168–170° C. | 3.21 (S, in $CCl_4$ + DMSO-$d_6$) |
| 112 | F | F | — | 4 | — | 0 | =CH— | 2,4-dichlorophenyl | mp. 174–179° C. | 3.20 (S, in Acetone-$d_6$) |
| 113 | F | F | 2-$CH_3$ | 4 | — | 0 | =C(CH$_3$)— | | | |
| 114 | F | F | — | 4 | — | 0 | =CH— | 4-methylphenyl | mp. 162–163° C. | 3.21 (S, in $CCl_4$) |
| 115 | F | F | 4-$CH_3$ | 3 | O | 1 | =CH— | 2-chloro-4-trifluoromethylphenyl | mp. 142–144° C. | 3.11 (S, in $CCl_4$) |
| 116 | F | F | — | 4 | O | 1 | =CH— | 4-trifluoromethoxyphenyl | | |
| 117 | F | F | — | 4 | — | 0 | =CH— | 4-trifluoromethoxyphenyl | | |
| 118 | F | F | 3-$CH_3$ | 4 | O | 1 | =CH— | 2-chloro-4-trifluoromethoxyphenyl | | |
| 119 | F | F | 3,5-$(CH_3)_2$ | 4 | O | 1 | =CH— | 2-chloro-4-trifluoromethoxyphenyl | | |
| 120 | F | F | 3-$CO_2$—Na | 4 | O | 1 | =CH— | 2-chloro-4-trifluoromethylphenyl | | |
| 121 | F | F | 3-$CO_2$—$C_2H_5$ | 4 | O | 1 | =CH— | 2-chloro-4-trifluoromethylphenyl | | |
| 122 | F | F | 4-Cl | 3 | O | 1 | =CH— | 2-chloro-4-trifluoromethylphenyl | | |
| 123 | F | F | — | 4 | O | 1 | =CH— | 2-chloro-5-trifluoromethyl-3-pyridyl | | |
| 124 | F | F | 3-F | 4 | — | 0 | =CH— | 4-trifluoromethylphenyl | | |
| 125 | F | F | — | 4 | —N(CH$_3$)— | 1 | =CH— | 3-chloro-5-trifluoromethyl-2-pyridyl | mp. 147° C. | |
| 126 | F | F | — | 4 | —N(CH$_3$)— | 1 | =CH— | 2-chloro-4-trifluoromethylphenyl | mp. 98–100°0 C. | |

(*1) $^1$H-NMR: Chemical shift value of the methyl group substituted at the urea moiety. Tetramethylsilane was used as the internal standard. S is the abbreviation of singlet.

The compounds of the present invention show excellent activities as active ingredients for pesticides, especially insecticides, acaricides and pesticides for slugs and snails. For instance, they are effective against plant parasitic mites such as two-spotted spider mite (*Tetranychus urticae*), carmine spider mite (*Tetranychus cinnabarinus*), citrus red mite (*Panonychus citri*) or bulb mite (*Rhizoglyphus echinopus*); agricultural insect pests such as diamondback moth (*Plutella xylostella*), cabbage armyworm (*Mamestra brassicae*), common cutworm (*Spodoptera litura*), colorado potato beetle (*Leptinotarsa decemlineata*), codling moth (*Laspeyresia pomonella*), ballworm (*Heliothis zea*), tobacco budworm (*Heliothis virescens*), ball weevil (*Anthonomus grandis*), gypsy moth (*Lymantria dispar*), cucurbit leaf beetle (*Aulaco-

*phora femoralis*), thrips, grasshoppers, anthomyiid flies, scarabs, black cutworm (*Agrotis ipsilon*) or cutworm (*Agrotis segetum*), hygienic pests such as cockroaches, housefly (*Musca domestica*) or house mosquito (*Culex pipiens pallens*); stored grain insect pests such as angoumois grain moth (*Sitotroqa cerealella*), confused flour beetle (*Tribolium confusum*) or mealworms; household goods insect pests such as casemaking clothes moth (*Tinea pellionella*), black carpet beetle (*Anthrenus scrophularidae*), or subterranean termites; and other parasites on domestic animals such as flies. Further, they are effective also against mites having the resistance to dicofol and organophosphorus insecticides and against insect pests such as diamondback moth and housefly having the resistance to organophosphorus and/or pyrethroid insecticides. Furthermore, they are effective also against slugs and snails.

The compounds of the present invention exhibit particularly excellent larvicidal activities against larvae of insects and mites. However, they are effective also against adults of pests. Namely, they inhibit the reproduction of pests in such a manner that when taken in by the adult pests, the compounds of the present invention are effective to destroy the ability of the adult pests to lay eggs or to prevent laid eggs from hatching. Thus, they show excellent pesticidal effects over a long period of time.

The compounds of the present invention serve mainly as stomach poison. Therefore, they do not affect beneficial organisms including beneficial insects that do not feed on crop plants. Further, they will be decomposed satisfactorily in soil, and they do not affect aquatic beneficial organisms. Thus, they have preferable characteristics as pesticides.

When used as active ingredients for pesticides, the compounds of the present invention may be formulated together with agricultural adjuvants into various forms such as liquids, dusts, granules, wettable powders, emulsifiable concentrates, flowables, aerosols, pastes or ultra low-volume formulations just like conventional agricultural chemicals. When such formulations are to be actually used, they may be used as they are or after being diluted with suitable diluents such as water to a predetermined concentration.

Such formulations are usually composed of 0.5–90 parts by weight of active ingredient and 10–99.5 parts by weight of agricultural adjuvants.

As the agricultural adjuvants, there may be mentioned carriers, emulsifiers, suspending agents, dispersants, extenders, penetrating agents, wetting agents, thickeners or stabilizers. They may be added as the case requires. The carriers may be divided into solid carriers and liquid carriers. As the solid carriers, there may be mentioned powders of animal and plant origin, such as starch, activated carbon, soybean flour, wheat flour, wood powder, fish powder or milk powder; or mineral powders such as talc, kaolin, bentonite, calcium carbonate, zeolite, diatomaceous earth, fine silica, clay, alumina or sulfur powder. As the liquid carriers, there may be mentioned water; alcohols such as methyl alcohol or ethylene glycol; ketones such as acetone or methyl ethyl ketone; ethers such as dioxane or tetrahydrofuran; aliphatic hydrocarbons such as kerosine or the like; aromatic hydrocarbons such as xylene, trimethylbenzene, tetramethylbenzene, cyclohexane or solvent naphtha; halogenated hydrocarbons such as chloroform or chlorobenzene; acid amides such as dimethylformamide; esters such as ethyl acetate or glycerine ester of a fatty acid; nitriles such as acetonitrile; or sulfur-containing compounds such as dimethyl sulfoxide.

Further, the compounds of the present invention may be used in combination with other agricultural chemicals such as insecticides, miticides, nematocides, fungicides, antiviral agents, attractants, herbicides or plant growth regulators, as the case requires. In some cases, the effectiveness will be improved by such combination.

For instance, as such insecticides, miticides or nematocides, there may be mentioned organophosphorus compounds, carbamate compounds, organic chlorine compounds, organic metal compounds, pyrethroide compounds, benzoyl urea compounds, other compounds and juvenile hormone-like compounds. Further, microbial insecticide such as *Bacillus thuringiensis* agent or nuclear polyhedrosis virus may also be used in combination with the compounds of the present invention.

As the fungicides, there may be mentioned organophosphorus compounds, organic chlorine compounds, N-halogenothioalkyl compounds, dicarboxy imide compounds, benzimidazole compounds, azole compounds, carbinol compounds, benzanilide compounds, acylalanine compounds, pyridinamine compounds, and other compounds.

The pesticides of the present invention are effective for the control of various noxious insects, noxious mites, and other noxious pests. They are applied in an active ingredient concentration of from 1 to 20,000 ppm, preferably from 20 to 2,000 ppm. The active ingredient concentration may be optionally changed depending upon the formulation, the manner, purpose, timing or place of the application and the condition of the insect pests. For instance, aquatic noxious insects can be controlled by applying the formulation having the above-mentioned concentration to the site of the outbreak, and thus, the concentration of the active ingredient in water is less than the above-mentioned range.

The amount of the application of the active ingredient per unit surface area is usually from about 0.1 to 5,000 g, preferably from 5 to 1,000 g, per 10a. However, in a certain special case, the amount of the application may be outside the above range.

Various formulations containing the compounds of the present invention or their diluted compositions may be applied by conventional methods for application which are commonly employed, such as spraying (e.g. spraying, jetting, misting, atomizing, powder or grain scattering or dispersing in water), soil application (e.g. mixing or drenching), surface application (e.g. coating, powdering or covering) or impregnation to obtain poisonous feed. Further, it is possible to feed domestic animals with a feed containing the above active ingredient and to control the outbreak or growth of pests, particularly insect pests, with their excrements. Furthermore, the active ingredient may also be applied by a so-called ultra low-volume application method. In this method, the composition may be composed of 100% of the active ingredient.

Now, Test Examples of the present invention will be described.

TEST EXAMPLE 1

Miticidal test against two-spotted spider mite

Each formulation containing an active ingredient was dispersed in water to obtain a dispersion of each active ingredient having a concentration of 800 or 200 ppm. Each of French bean seedlings with only on primary leaf left, was transplanted to a cup having a diameter of 7 cm and a height of 4 cm. About 30 larvae and nimphs of two-spotted spider mite (*Tetranychus urticae*) were infested to the leaf of the French bean. Then, the French bean was dipped in the dispersion having the concentration of 800 ppm or 200 ppm for about 10 seconds, then dried in air and kept in a constant temperature chamber with lightening at 26° C. On the 5th day after the treatment, dead mites were counted, and the mortality was calculated by the following equation:

$$\text{Mortality (\%)} = \frac{\text{Number of dead mites}}{\text{Number of total mites}} \times 100$$

The results are shown in Table 4.

TABLE 4

| Compound No. | Mortality (%) 800 ppm | 200 ppm |
| --- | --- | --- |
| 4 | 90 | — |
| 12 | 100 | 100 |
| 13 | — | 99 |
| 18 | — | 100 |

TEST EXAMPLE 2

Insecticidal test against diamondback moth

Each formulation containing an active ingredient was dispersed in water to obtain a dispersion of each active ingredient having a concentration of 10 ppm. Leaves of cabbage were dipped in the respective dispersions for about 10 seconds, and then dried in air. A sheet of moistened filter paper was placed in a Petri dish having a diameter of 9 cm, and the dried leaves of cabbage were put on the filter paper. Larvae of diamondback moth (*Plutella xylostella*) in second or third instar were released on the leaves, and the Petri dishes were covered and kept in a constant temperature chamber with lightening at a temperature of 26° C. On the 7th day after release, dead insects were counted, and the mortality was calculated by the following equation:

The mortality was 100% with each of Compounds Nos. 1–10, 12–36, 39, 41, 43–47, 49–57, 62–74, 76–77, 80–86, 108–109, 111–115, 125 and 126, and 90% with each of Compounds Nos. 40 and 75.

$$\text{Mortality (\%)} = \frac{\text{Number of dead insects}}{\text{Number of total insects}} \times 100$$

TEST EXAMPLE 3

Insecticidal test against common cutworm

The tests were conducted in the same manner as in Test Example 2 except that larvae of common cutworm (*Spodoptera litura*) in second or third instar were used instead of larvae of the diamondback moth in second or third instar, and the concentration of the active ingredient was changed from 10 ppm to 800 ppm or 1 ppm.

At the concentration of 800 ppm, the mortality was 100% with each of Compounds Nos. 1–86, 108–109, 111–115, 125 and 126.

At the concentration of 1 ppm, the mortality was 100% with each of Compounds Nos. 1–8, 11–27, 29, 31–36, 39–41, 43–47, 49–60, 62–63, 65–66, 68–72, 74, 76–78, 80, 82–86, 108–109, 111–113, 115, 125 and 126, and 90% with each of Compounds Nos. 64 and 75.

TEST EXAMPLE 4

Larvicidal test against larvae of house fly

Powder feed for test animals (manufactured by Oriental Kobo Kogyo K.K.) and bran were mixed in a weight ratio of 1:1 and pulverized, and 10 g of the mixture was packed in an ice cream cup. Each of the formulations containing the active ingredients, was dispersed in water, and 10 ml of the dispersion was added to the mixture in the ice cream cup and thoroughly mixed to adjust the concentration of the active ingredient to 10 ppm. Into the ice cream cup, 20 larvae of house fly (*Musca domestica*) in second instar were released, and kept in a constant temperature chamber with lightening at 26° C. On the 10th day after the release, the emerged adults were counted, and the mortality was calculated in accordance with the following equation.

$$\text{Mortality (\%)} = \frac{\text{Number of released larvae} - \text{Number of emerged adults}}{\text{Number of released larvae}} \times 100$$

The mortality was 100% with each of Compounds Nos. 1–5, 12–13 and 24, and 90% with Compound No. 6.

TEST EXAMPLE 5

Larvicidal test against larvae of house mosquito

Two hundreds ml of a diluted solution containing 2.5 ppb of each active ingredient was poured into a jar and 20 larvae of house mosquito (*Cullex pipiens pallens*) were released into the jar. Then, the jar was kept in a constant temperature chamber with lightening at 26° C. Larvae were fed every other day with 1–2 mg of powdered feed. On the 9th day after the release, dead insects were counted, and the mortality was calculated in the same manner as in Test Example 2. The results are shown in

TABLE 5

| Compound No. | Mortality (%) 2.5 ppb |
| --- | --- |
| 1 | 100 |
| 2 | 90 |
| 3 | 100 |
| 4 | 100 |

TEST EXAMPLE 6

Egg hatch inhibition test by the treatment of adults of house fly

Sugar and skim milk were mixed in a weight ratio of 1:1, and 2 g of the mixture was put into a Petri dish having a diameter of 5.5 cm. 0.5 ml of an acetone solution containing the active ingredient was added to the mixture in the Petri dish. After acetone evaporated, the treated mixture was thoroughly mixed, and the concentration of the active ingredient was adjusted to 100 µg/g. Twenty non-mating females of house fly (*Musca domestica*) were allowed to feed on the poisoned diet (the treated mixture) in a cage. After 3 days, the diet was changed to the untreated mixture, then 20 non-mating males were released into the cage for mating. On the 3rd day after release, a cup of the medium for rearing fly larvae was set in the cage for oviposition for 7 hours. The egg laid on the medium were collected and kept on the moistened filter paper in a Petri dish. One day later, unhatched eggs were assessed and the ratio of the egg hatch inhibition (REHI) was calculated by the following equation:

$$REHI\ (\%) = \frac{\text{Number of unhatched eggs}}{\text{Number of collected eggs}} \times 100$$

The egg hatch inhibition was 100% with each of Compounds Nos. 1, 5, 12–13, 15, 20, 24, 29 and 31, and 88% with Compound No. 3.

TEST EXAMPLE 7

0.5 ml of a 200 ppm dispersion in acetone of each compound (100 μg) was added to the flask by means of a pipet (to a concentration of 5 ppm). The flask was closed and thoroughly shaked, and the soil attached to the closure was washed into the flask with a small amount of water. Then, the top of the flask was covered with an aluminum foil, and the flask was subjected to incubation in a growth cabinet (30° C., humidity: 60%, continuously lighted with a fluorescent lamp with 9,000 lux). 20 Days later, the total 20 g of the soil was subjected to analysis, and the remaining amount of the compound was measured. The results of tests I, II and III are shown in Table 6.

TABLE 6

| Compound Structure | R | Insecticidal activity C-value (ppm) | | $EC_{50}$ (ppb) of *Daphnia magna* Straus | Remaining rate in the soil (%) |
|---|---|---|---|---|---|
| | | Common cutworm | Diamondback moth | | |
| [structure 1] | H | 0.04 | 0.08 | <0.4 | 91 |
| | $CH_3$ | 0.04 | 0.08 | 150 | 76 |
| [structure 2] | H | 0.08 | 0.08 | <0.4 | 84 |
| | $CH_3$ | 0.02 | 0.02 | 50 | 49 |
| [structure 3] | H | 0.6 | 0.3 | <0.8 | 77 |
| | $CH_3$ | 0.04 | 0.02 | 150 | 45 |

I. Insecticidal tests

In the same manner as in Test Examples 2 and 3, insecticidal tests against diamondback moth and common cutworm were conducted with respect to each compound, and the minimum concentrations at which no less than 90% of insects are killed (hereinafter referred to as C-value), were obtained.

II. Acute Immobilisation Test against *Daphnia magna* Straus

An acetone solution of each compound was dispersed in water to obtain test solutions having various concentrations of the active ingredient. 250 ml of each test solution was introduced into a 430 ml glass beaker. Into each beaker, 10 first instar larvae born within 24 hours were released and kept at the solution temperature of 23±1° C. The immobilisation up to 48 hours after the release of the larvae was investigated in accordance with the OECD test guideline. The test was repeated 2–3 times in two series for each concentration. The 50% immobilisation concentration ($EC_{50}$, ppb) was obtained by Probit method.

III. Residual test in soil

Upland soil (volcanic ash soil) was screened through a sieve with a mesh size of 5 mm, and 20 g by dry weight basis of the soil was put into a 100 ml Erlenmeyer flask. Then, distilled water was introduced to simulate an irrigated condition with a water depth of 1 cm. An aluminum foil was put on the top of the flask, and the flask was left to stand still for 1 week in an incubator (dark place) at 30° C.

Now, the Formulation Examples of the present invention will be described. However, the compounds of the present invention, the amount of the active ingredients or the types of the formulations are not restricted to these specific Examples.

FORMULATION EXAMPLE 1

| (a) Compound No. 18 | 20 Parts by weight |
| (b) Kaoline | 72 Parts by weight |
| (c) Sodium lignin sulfonate | 8 Parts by weight |

The above components are uniformly mixed to obtain a wettable powder.

FORMULATION EXAMPLE 2

| (a) Compound No. 24 | 5 Parts by weight |
| (b) Talc | 95 Parts by weight |

The above components are uniformly mixed to obtain a dust.

FORMULATION EXAMPLE 3

| (a) Compound No. 3 | 20 Parts by weight |
| (b) N,N'-dimethylformamide | 20 Parts by weight |
| (c) Polyoxyethylenealkylphenyl ether | 10 Parts by weight |
| (d) Xylene | 50 Parts by weight |

The above components are uniformly mixed and dissolved to obtain an emulsifiable concentrate.

FORMULATION EXAMPLE 4

| | | |
|---|---|---|
| (a) | Kaoline | 78 Parts by weight |
| (b) | Sodium lignin sulfonate | 2 Parts by weight |
| (c) | Polyoxyethylenealkylaryl sulfate | 5 Parts by weight |
| (d) | Fine silica powder | 15 Parts by weight |

A mixture of the above components and Compound No. 31 were mixed in a weight ration of 4:1 to obtain a wettable powder.

FORMULATION EXAMPLE 5

| | | |
|---|---|---|
| (a) | Compound No. 46 | 40 Parts by weight |
| (b) | Oxylated polyalkylphenol phosphate-triethanolamine | 2 Parts by weight |
| (c) | Silicon | 0.2 Part by weight |
| (d) | Xanthan gum | 0.1 Part by weight |
| (e) | Ethylene glycol | 5 Parts by weight |
| (f) | Water | 52.7 Parts by weight |

The above components are uniformly mixed and pulverized to obtain a flowable.

FORMULATION EXAMPLE 6

| | | |
|---|---|---|
| (a) | Compound No. 3 | 50 Parts by weight |
| (b) | Oxylated polyalkylphenyl phosphate-triethanolamine | 2 Parts by weight |
| (c) | Silicon | 0.2 Part by weight |
| (d) | Water | 47.8 Parts by weight |

The above components are uniformly mixed and pulverized to obtain a base liquid, and

| | | |
|---|---|---|
| (e) | Sodium polycarboxylate | 5 Parts by weight |
| (f) | Anhydrous sodium sulfate | 42.8 Parts by weight | were added, and the mixture was uniformly mixed and dried to obtain a dry flowable.

FORMULATION EXAMPLE 7

| | | |
|---|---|---|
| (a) | Compound No. 49 | 5 Parts by weight |
| (b) | Glycerin | 20 Parts by weight |
| (c) | Milk powder | 3 Parts by weight |
| (d) | Fish powder | 72 Parts by weight |

The above components are uniformly kneaded to obtain a paste.

FORMULATION EXAMPLE 8

| | | |
|---|---|---|
| (a) | Compound No. 57 | 5 Parts by weight |
| (b) | Wheat bran | 10 Parts by weight |
| (c) | Rice bran | 80 Parts by weight |
| (d) | Molasses | 5 Parts by weight |

The above components are uniformly mixed and kneaded together with a small amount of water, and then the mixture was molded by extrusion molding into a granular form, followed by drying to obtain granules.

FORMULATION EXAMPLE 9

| | | |
|---|---|---|
| (a) | Compound No. 76 | 2.5 Parts by weight |
| (b) | N-methyl-2-pyrrolidone | 2.5 Parts by weight |
| (c) | Soybean oil | 95.0 Parts by weight |

The above components are uniformly mixed and dissolved to obtain an ultra low-volume formulation.

FORMULATION EXAMPLE 10

| | | |
|---|---|---|
| (a) | Compound No. 29 | 5 Parts by weight |
| (b) | N,N'-dimethylformamide | 5 Parts by weight |
| (c) | Polyoxyethylenealkylaryl ether | 10 Parts by weight |
| (d) | Xylene | 80 Parts by weight |

The above components are uniformly mixed to obtain an emulsifiable concentrate.

We claim:

1. A benzoylurea compound having the formula:

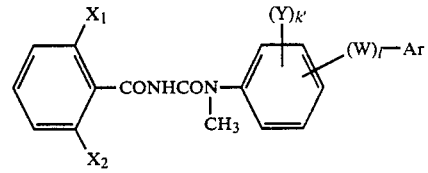

wherein each of $X_1$ and $X_2$ is a hydrogen atom, a halogen atom or a methyl group, provided that $X_1$ and $X_2$ are not simultaneously hydrogen atoms, Y is, independently, a hydrogen atom, a halogen atom, a $C_1$-$C_6$ alkyl group which may be substituted by halogen, a —$CO_2R_1$ group wherein $R_1$ is a hydrogen atom, an alkali metal atom, a $C_1$-$C_6$ alkyl group, or a —$OR_1$ group wherein $R_1$ is as defined above, W is an oxygen atom, a sulfur atom or —$NR_1$—wherein $R_1$ is as defined above, k' is an integer of from 1 to 4, l is 0 or 1, and AR is

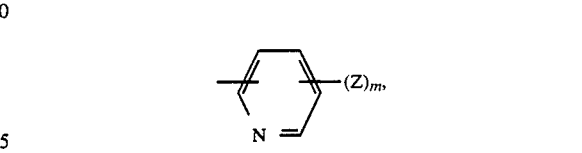

wherein Z is independently, a hydrogen atom, a halogen atom, a $C_1$-$C_6$ alkyl group which may be substituted by halogen, a nitro group, a cyano group or a —$S(0)_nR_2$ group, wherein $R_2$ is a $C_1$-$C_6$ alkyl group which may be substituted by halogen, n is 0, 1 or 2, and m' is an integer from 1 to 4, or a salt thereof.

2. The compound according to claim 1, which is N-[4-(3-chloro-5-trifluoromethyl-2-pyridyloxy)-2,3-difluorophenyl]-N'-(2,6-difluorobenzoyl)-N-methylurea, N-[3-chloro-4-(3-chloro-5trifluoromethyl-2-pyridyloxy)phenyl]-N'-(2,6-difluorobenzoyl)-N-methylurea, N-[4-(3-chloro-5-trifluoromethyl-2-pyridyloxy)-2,5-dimethylphenyl]-N'-(2,6-difluorobenzoyl)-N-methylurea, N-[3-chloro-4-(3-chloro-5-trifluoromethyl-2-pyridyloxy)-2-fluorophenyl]-N'-(2,6-difluorobenzoyl)-N-methylurea, N-[4-(3-chloro-5-trifluoromethyl-2pyridyloxy)phenyl]-N'-(2-chlorobenzoyl)-N-methylurea, N-[4-(3-chloro-5-trifluoromethyl-2-pyridyloxy)-2-methylphenyl]-N'-(2,6-difluorobenzoyl)-N-methylurea, N-{4-[3-chloro-5-trifluoromethyl-2-pyridyloxy]-3-fluorophenyl}-N'-(2,6-difluorobenzoyl)-N-methylurea, or N-{4-[3-chloro-5-trifluoromethyl-2-pyridyloxy]-3-methylphenyl}-N'-(2-chlorobenzoyl)-N-methylurea.

3. The compound according to claim 1, which has the formula:

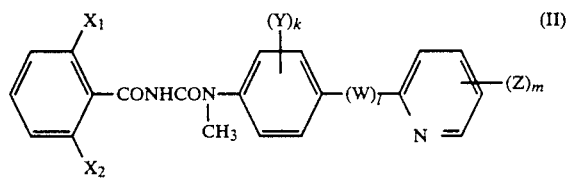

wherein $X_1$, $X_2$, Y, W, k, l, Z, and m are as defined above, or a salt thereof.

4. The compound according to claim 1, wherein each of $X_1$ and $X_2$ is a hydrogen atom or a halogen atom, provided at least one of them is a halogen atom.

5. The compound according to claim 1, wherein Y is independently a hydrogen atom, a halogen atom, alkyl group which may be substituted by halogen, or a $-CO_2R_1$ group wherein $R_1$ is as defined above.

6. The compound according to claim 1, wherein Z is independently a hydrogen atom, a halogen atom, a trifluoromethyl group, a trifluoromethoxy group or a $-S(0)_nCF_3$ group wherein n is as defined above.

7. The compound according to claim 1, which is N-[3,5-dichloro-4-(3-chloro-5-trifluoromethyl-2-pyridyloxy)phenyl]-N'-(2,6-difluorobenzoyl)-N-methylurea.

8. A pesticidal composition comprising a pesticidally effective amount of a benzoylurea compound as defined in claim 1, and an agriculturally acceptable adjuvant.

9. The pesticidal composition according to claim 8, which comprises from 0.5 to 90 parts by weight of the benzoylurea compound and from 10 to 99.5 parts by weight of the adjuvant.

* * * * *